United States Patent [19]
Gaffney et al.

[11] Patent Number: 5,462,971
[45] Date of Patent: * Oct. 31, 1995

[54] PROCESS FOR TREATING POLYETHER POLYOLS

[75] Inventors: Anne M. Gaffney, West Chester; C. Andrew Jones, Newtown Square, both of Pa.

[73] Assignee: ARCO Chemical Technology, L.P., Greenville, Del.

[*] Notice: The portion of the term of this patent subsequent to Mar. 9, 2010, has been disclaimed.

[21] Appl. No.: 197,039

[22] Filed: Feb. 16, 1994

[51] Int. Cl.$^6$ .................................................. C08J 11/04
[52] U.S. Cl. .................................................. 521/40
[58] Field of Search .................................................. 521/40

[56] References Cited

U.S. PATENT DOCUMENTS

| | | | |
|---|---|---|---|
| 4,108,730 | 8/1979 | Chen et al. | 201/2.5 |
| 4,175,211 | 11/1979 | Chen et al. | 585/241 |
| 4,243,560 | 1/1981 | Balestrini | 260/2.3 |
| 4,439,616 | 3/1984 | Singh et al. | 560/25 |
| 4,584,421 | 4/1986 | Saito et al. | 585/241 |
| 4,851,601 | 7/1989 | Fukuda et al. | 585/241 |
| 5,079,385 | 1/1992 | Wu | 585/241 |
| 5,192,809 | 3/1993 | Jones et al. | 521/40 |
| 5,274,004 | 12/1993 | van der Wal | 521/49.5 |
| 5,288,934 | 2/1994 | Broqueville | 585/241 |

OTHER PUBLICATIONS

Mordi, et al. J. Chem. Soc. Chem. Commun. 374(1992) "Gasoline Range Chemicals from Zeolite–Catalysed Thermal Degradation of Polypropylene".

Primary Examiner—James J. Seidleck
Assistant Examiner—Mary Critharis
Attorney, Agent, or Firm—William C. Long

[57] ABSTRACT

The invention provides a process for the fluid bed cracking of polyether polyols to volatile lower molecular weight products.

6 Claims, 1 Drawing Sheet

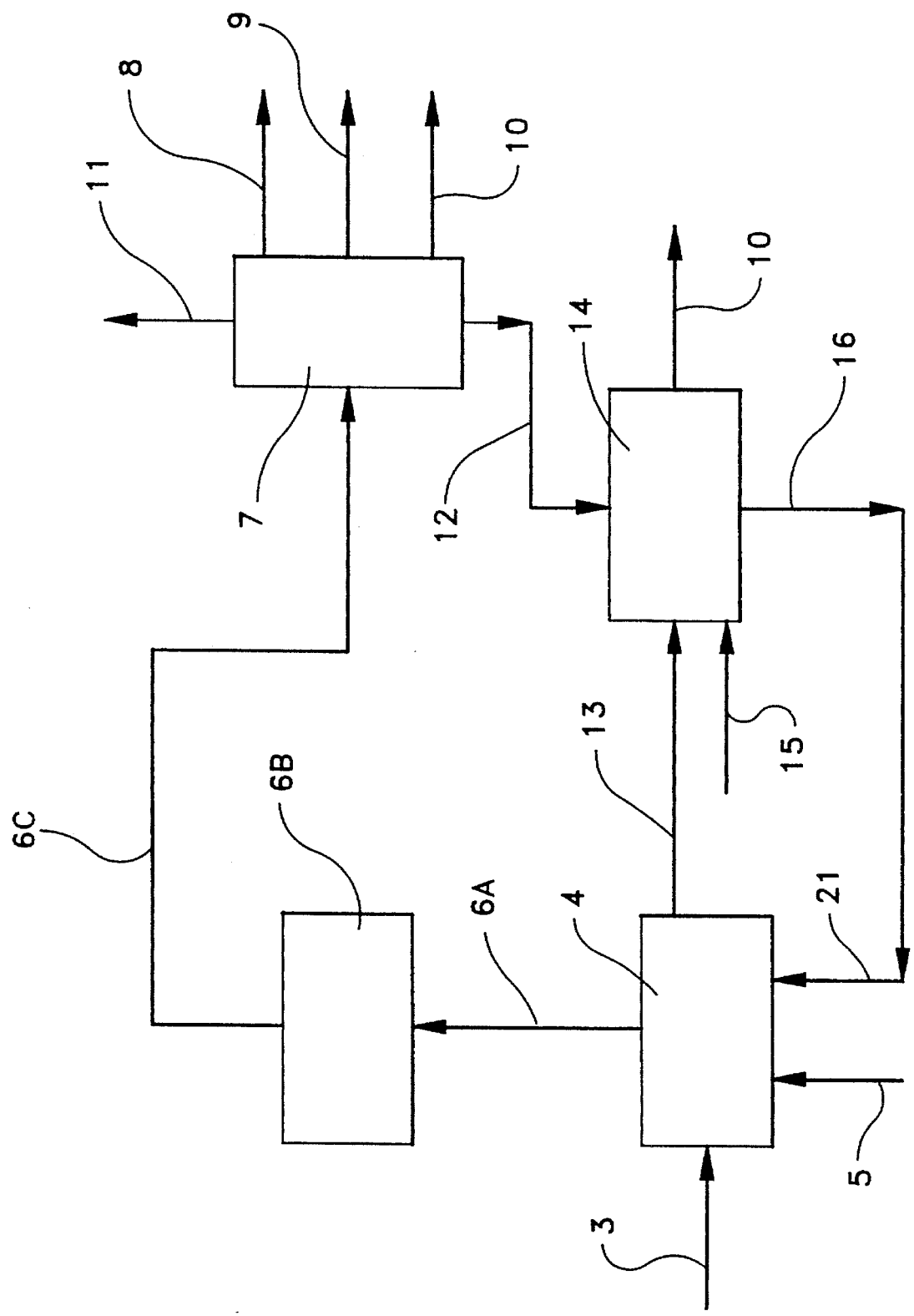

PROCESS FOR TREATING POLYETHER POLYOLS

FIELD OF THE INVENTION

This invention relates to methods whereby polyether polyols such as those recoverable as waste components may be converted into volatile lower molecular weight compounds useful as chemical intermediates, solvents, or fuels.

BACKGROUND OF THE INVENTION

In view of the increasing importance of polymers as substitutes for conventional materials of construction such as glass, metal, paper, and wood, the perceived need to conserve non-renewable resources such as petroleum and the dwindling amount of landfill capacity available for the disposal of waste products, considerable attention has been devoted in recent years to the problem of recovering, reclaiming, recycling or in some way reusing waste polymers.

It has also been proposed to pyrolyze or catalytically crack thermoplastic polymers so as to convert the high molecular weight polymer into volatile compounds having much lower molecular weight. The volatile compounds, depending on the process employed, may be either relatively high boiling liquid hydrocarbons useful as fuel oils or fuel oil supplements or light to medium boiling hydrocarbons useful as gasoline-type fuels or as chemical "building blocks". For example, polystyrene may be pyrolytically cracked so as to provide a substantial yield of styrene monomer.

SUMMARY OF THE INVENTION

This invention provides a process for reclaiming a polyether polyol comprising the steps of:

(a) Heating the polyether polyol and a zeolite-containing particulate catalyst in a fluidized bed reaction zone at a temperature effective to produce a volatile organic component, and a spent catalyst component having carbon deposited thereon;

(b) Withdrawing a first stream comprising the volatile organic component from the reaction zone;

(c) Withdrawing a second stream comprising spent catalyst; and (d) Heating the second stream in a regeneration zone in the presence of oxygen at a temperature effective to convert the carbon to carbon dioxide and water and to regenerate the catalyst.

In one embodiment, the present invention provides a process for treating a polyether polyol comprising the steps of:

(a) Contacting the polyether polyol and a zeolite-containing particulate catalyst in a dense fluidized bed reaction zone at a temperature of from about 150° C. to 700° C. to produce a volatile organic component and a spent catalyst component;

(b) Withdrawing a first stream comprising the volatile organic component from the reaction zone;

(c) Withdrawing a second stream comprising spent catalyst from the reaction zone;

(d) Heating the second stream in a regeneration zone in the presence of oxygen at a temperature of from about 250° C. to 700° C. to convert carbon deposited on the catalyst to carbon dioxide and thus regenerate the catalyst; and (e) Introducing the regenerated catalyst to the reaction zone.

BRIEF DESCRIPTION OF THE INVENTION

FIG. 1 is a schematic flow diagram of a preferred embodiment of the process of the invention.

DETAILED DESCRIPTION OF THE INVENTION

Any polyether polyol polymer may be employed in the process of this invention including polymers which are already crosslinked.

A distinct advantage of the process of this invention is that mixtures of polyether polyols polymers may be utilized as the feed. Another advantage of the invention is that thermoplastic polymers such as polyethylene, polypropylene, polystyrene, polyamide (nylon), polyvinyl chloride, polyethylene terephthalate, polybutylene terephthalate, polymethyl methacrylate, polyphenylene oxide, styrene/maleic anhydride copolymer, ABS and MBS resins, thermoset polyurethanes, and the like and elastomers and rubbers such as natural rubbers, polybutadiene, polyolefin rubbers, butyl rubbers, neoprenes, polyisobutylene, silicone rubbers, nitrile rubbers, styrene-butadiene or styrene-isoprene rubbers, and acrylate rubbers may also be employed as admixtures with the polyether polyols polymer, since such thermoplastics, thermosets and rubbers will be successfully cracked or converted to useful volatile organic compounds simultaneous with transformation of the polyether polyols polymer. Moreover, cellulose-based organic wastes such as paper or wood will not adversely affect the process of this invention. Thus, the need for tedious and expensive separation steps prior to introduction of the feed into the reaction zone is minimized.

The polyether polyols which are converted in accordance with the present invention are generally those having a molecular weight in the range of about 200 to 15,000. The materials can be derived from polyurethanes after hydrolysis, glycolysis, methanolysis, and the like of polyurethanes. Recycled and off grade polyether polyols can be used. Polyol polyesters can be employed.

Generally, the materials which are converted in accordance with the invention are characterized by recurring $C_2$–$C_4$ alkylene oxide groups, ie.

—$(AO)_n$—wherein A is a $C_2$–$C_4$ alkylene group and n is preferably 3 to 200.

The most commonly available polyether polyols are those derived from glycerin having the formula,

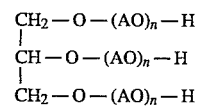

where A is a $C_2$–$C_4$ alkylene group and each n is at least 1 with the total of the n's being up to about 200.

Derivatives of ethylene oxide and propylene oxide are particularly useful.

The zeolite containing particulate catalyst component of this invention may be either an unbound (unsupported) zeolite or a catalyst wherein a binder (co-gel) or support is used in combination with a zeolite. Such zeolite binders or supports are well known in the art, as are methods of preparing bound or supported zeolite catalysts. Illustrative binders include silica, alumina, silica-alumina, silica-titania, silica-thoria, silica-magnesia, silica-zironia, silica-beryllia, and ternary compositions of silica with other refractory oxides. Also useful as binders or matrix materials are clays such as montmorillonites, kaolins, bentonites, halloysites, dickites, nacrites, and anaxites. The proportion of zeolite-:binder may range from 99:1 to 1:99, but preferably is from 5:95 to 80:20.

In this context, the term "zeolite" encompasses not only the true zeolites, which are characterized by having crystalline aluminosilicate three-dimensional structures arising from a framework of $[SiO_4]^{4-}$ and $[AlO_4]^{5-}$ coordination polyhedra linked through their corners, but also the "zeotypes", which are crystalline silicates which resemble true zeolite in structure and properties but which are essentially alumina-free. Zeotypes are exemplified by crystalline silica polymorphs (e.g., silicates, disclosed in U.S. Pat. No. 4,061,724 and organo-silicates, disclosed in U.S. Pat. No. Re. 29,948), chromia silicates (e.g., CZM), ferrosilicates and galliosilicates (disclosed in U.S. Pat. No. 4,238,318), and borosilicates (disclosed in U.S. Pat. Nos. 4,226,420, 4,269,813) and 4,327,236). The use of crystalline aluminosilicate zeolite is preferred, however. Such zeolite are well known and are described in Szostak, *Molecular Sieves: Principles of Synthesis and Identification* Van Nostrand Reinhold (1989), Dyer, *An Introduction to Zeolite Molecular Sieves* Wiley (1988), Jacobs, *Carboniogenic Activity of Zeolite Elseviar* (1977), Breck, *Zeolite Molecular Sieves: Structure, Chemistry and Use* Wiley (1974), and Breck et al. "Molecular Sieves", in *Kirk-Othmer Encyclopedia of Chemical Technology* Vol. 15, p. 638. Zeolite of both natural and synthetic origin may be employed. Preferred zeolite for use in this invention include ZSM-5 (see U.S. Pat. Nos. 3,702,886 and 3,770,614), ZSM-11 (see U.S. Pat. No. 3,709,979), ZSM-12 (see U.S. Pat. No. 3,832,449), ZSM-21 and ZSM-38 (see U.S. Pat. No. 3,958,758), ZSM-23 (see U.S. Pat. No. 4,076,842), and ZSM-35 (see U.S. Pat. No. 4,016,246). Zeolite containing group 5A elements, especially phosphorus containing zeolite, are particularly preferred for use since it has been unexpectedly found that this class of zeolite is very tolerant of steam and tends to retain an unusually high degree of activity and selectivity in the presence of steam. This is an important advantage since steam is a preferred carrier gas for use in the process of this invention. Zeolite catalysts containing Group VA elements are describes in U.S. Pat. Nos. 3,977,832, 3,925,298, and 4,379,761, for example and in Vedrine, *J. Catal.* 73, 147 (1982) Boron containing zeolite or borosilicates (as described in U.S. Pat. Nos. 3,328,119, 4,029,716, 4,078,009, 4,269,813 and 4,656,016 and European Patent Publication Nos. 77,946 and 73,482) are also especially preferred for use in view of the fining that such catalysts similarly show extremely good steam tolerance. The teachings of each of the foregoing patents are incorporated herein by reference in their entirety. Illustrative boron containing zeolite catalyst suitable for use include "AMS-1B", a borosilicate having a ZSM-5 structure available from Amoco.

Also suitable for use will be zeolite catalysts loaded or doped with Group VIII metals such as platinum and palladium to help carry out secondary functions such as hydrogenation or hydrogenolysis in addition to the basic cracking reaction. Such bifunctional zeolite catalysts are well known and are described, for example, in Chapter V of Jacobs, *Carboniogenic Activity of Zeolite*, Elseviar (1977).

It will also be desirable to utilize the acidic forms of zeolite such as the ZSM types and borosilicates. HZSM-5 is particularly useful.

Other representative zeolite catalysts suitable for use include zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,314,752), mordenite, chabazite, faujasite, erionite, offretite, and zeolite beta. The teachings of each of the foregoing patents are incorporated herein by reference in their entirety. Mixtures of zeolite catalysts may also be employed. The pore size of the zeolite may be varied to control the composition of the volatile organic component produced by cracking the thermoset polymer. Thus, the pore size may be either small (a pore/channel diameter <5 angstroms; generally, those zeolites having 8 tetrahedra constituting their pore defining ring), intermediate (a pore/channel diameter between 5–7 angstroms; generally, those zeolites having 10 tetrahedra or 12 puckered tetrahedra constituting their pore defining ring), or large (a pore/channel diameter >7 angstroms; generally, those zeolites having more than 12 tetrahedra in their pore defining ring). In general, the use of large pore size zeolite will favor the production of higher molecular weight, higher boiling volatile organic compounds.

The particle size of the zeolite-containing particulate catalyst should be selected such that the catalyst may be readily fluidized in the reaction zone. In general, the catalyst should have a particle size of from about 10 to 150 microns.

The accompanying drawing illustrates preferred embodiment of the process of the invention. Other embodiments will, however, be evident to those skilled in the art.

Waste polyether polyol polymer solution, which may be optionally admixed in any suitable ratio with other waste materials, is fed via line 3 to fluidized bed reaction zone 4.

The polyether polyol polymer solution is conveniently injected into zone 4 and contacted with the zeolite containing particulate catalyst in fluidized bed reaction zone 4 at a temperature effective to convert all or part of the polymeric portion of the particles into one or more volatile organic components. In general, this temperature will be from about 150° C. to 700° C., but preferably will be from about 200° C. to 450° C. The precise mechanism by which the transformation associated with the process of this invention takes place is not known, but it is postulated that the polymer undergoes a limited amount of preliminary pyrolysis or thermal cracking upon being exposed to the high temperature within the reaction zone whereby partial scission or breakdown of the polymer takes place. The thermal degradation products thereby produced are thought to be sufficiently mobile or volatile so as to be capable of intimate contact with the zeolite containing particulate catalyst, thereafter being cracked by action of the catalyst into even more volatile monomers and other low molecular weight organic species.

The reactor gas velocity is sufficient to maintain the catalyst and the polymer particles present in random motion. The velocity should be high enough to effectively carry over through line 6A a first stream comprising the volatile organic component generated in the process of this invention. A carrier gas may be introduced into the reaction zone in order to maintain the desired reactor velocity. The carrier gas, which may be introduced through line 5, for example, can be an inert gas such as nitrogen or helium, one or more light hydrocarbons such as methane, ethane, butanes or the like, steam (a preferred carrier gas) or some combination or mixture thereof.

The catalyst is deployed in a fluidized bed, preferably a dense or "fluffed" fluidized bed so as to minimize the distance between the polymer particles and the catalyst particles and to prevent the unconverted polymer particles from settling too rapidly to the bottom of the reaction zone, while at the same time promoting effective, rapid, and intimate mixing of the component present in the reaction zone. Methods and equipment for using a zeolite type catalyst in a fluid bed reactor are well known and are described, for example, in Venute et al., *Fluid Catalytic Cracking With Zeolite Catalysts*, Marcel Dekker (1979), Sterka, "Fluid Catalytic Cracking", in *Chemical and Process Technology Encyclopedia*, Considine, Ed., McGraw-Hill (1974) pp. 505–509, and Anonymous, "Fluidized Bed Operations", Ibid., pp. 509–511, incorporated herein by reference in their entirety. The average concentration of catalyst particles within the fluidized bed is preferably about 5 to 15 pounds per cubic foot. It is desirable to introduce the polymer into the reactor zone at a point near the top of the fluidized catalyst bed.

If desired, a catalyst separation zone 6B may be positioned such that products exiting the reaction zone 4 through line 6A are treated so as to remove any catalyst that may have been inadvertently carried over and to return this catalyst to the reaction zone. Catalyst separation zone 6B is suitably comprised of one or more cyclone vessels of the type commonly employed in fluid catalytic cracking processes.

The coke will typically be deposited on the surfaces of the spent catalyst. The spent catalyst will be lower in activity than the fresh catalyst. To regenerate the spent catalyst and to remove the coke from the spent catalyst so that the catalyst may be desirably reused or recycled, a second stream comprising the spent catalyst, and coke is withdrawn from the reaction zone 4 through line 13 and passed into regeneration zone 14, wherein the stream is heated in the presence of oxygen (supplied through line 15) at a temperature effective to convert the coke to carbon dioxide and water and to regenerate the catalyst. Preferably, the temperature in the regeneration zone is from about 250° C. to 700° C. (more preferably, from about 350° to 700° C.). An advantage of this process is that the heat generated in the catalyst regeneration step can be used in other steps of the process requiring the input of heat such as the fluidized bed reaction zone. The overall process is thus remarkably energy efficient. Gaseous products are removed through line 17, while the particulate product (regenerated catalyst essentially free of coke) is withdrawn via line 16.

The regenerated catalyst is fed back into reaction zone 4 through line 21 so as to replenish the supply of active catalyst in the reaction zone. The catalyst regeneration process is preferably carried out in a continuous manner.

The volatile organic component disengaged from catalyst separation zone 6B passes through line 6C to the product fractionator 7 and is separated into the desired product streams. The nature of these product streams will vary depending upon the composition of the polyether polyol polymer, the type of catalyst, and the operating conditions within the reactor zone, among other factors. Products of various volatility are withdrawn via lines 8, 9, 10 and 11. Gaseous products exit via line 11 while heavier products are withdrawn via lines 8, 9, and 10 in order of decreasing volatility. The bottoms fraction, which will be comprised of tarry substances of relatively high molecular weight as well as incompletely converted polymer or catalyst particles which are not recaptured and returned to the reactor zone by catalyst separation means 6B, is advantageously introduced through line 12 to regeneration zone 14. The gaseous fraction may be either employed as a carrier gas and introduced back into the reaction zone via line 5 or burned as a fuel to provide the heat necessary to maintain reaction zone 4 at the desired temperature.

If the volatile organic component which is generated in the process of this invention contains compounds having high value as chemical intermediates, these compounds may be recovered by conventional separation and fractionation means.

The present invention will be further described by the following specific examples, which are given by way of illustration and not as limitations of the scope of the invention.

In the following examples polyether polyol was cracked at elevated temperatures and the product distribution determined. Results as well as reaction conditions are given in the tables:

TABLE I

| Product[1] | Wt % Yield Example # | | | |
|---|---|---|---|---|
| | 1 | 2 | 3 | 4 |
| Methane | 0.3 | 0.1 | 0.2 | 0.1 |
| Ethane | 0.1 | 0.2 | Trace | 0.2 |
| Ethylene | 0.04 | 0.4 | 0.4 | 0.7 |
| Propane | 0.2 | 0.1 | 0.1 | 0.2 |
| Propylene | 1.4 | 1.3 | 1.8 | 1.8 |
| Acetaldehyde | 4.3 | 1.0 | 0.9 | 0.7 |
| Propionaldehyde | 2.7 | 61.3 | 81.6 | 39.8 |
| Acetone | 1.9 | 1.6 | 2.1 | 1.0 |
| 1,4-Dioxane | Trace | 0.6 | 4.2 | 1.7 |
| Propylene Oxide | 0.01 | 0.02 | 0 | 0.3 |
| n-propanol | 0.2 | 0.84 | 2.7 | 0.9 |
| i-propanol | 0.4 | 0.01 | 0.03 | 0.01 |
| Propylene Glycol | 0.9 | 1.5 | 2.5 | 1.7 |
| Dipropylene Glycol | 1.7 | 3.1 | 0.8 | 0.5 |
| Dioxalane | 0.1 | 2.1 | 2.3 | 2.1 |
| Lower MW Polyols[2] | 79.5 | 20.2 | 0 | 37.6 |
| G.C. lights[3] | 6.1 | 5.0 | 2.1 | 10.1 |
| $CO_2$ | 0.1 | 0.3 | 0.4 | 0.3 |
| Coke | 0.1 | 0.3 | 1.3 | 0.3 |
| Catalyst | None | A | A | A |
| Temp, °C. | 450 | 450 | 450 | 450 |
| Vol % Steam in $N_2$ Stream | 10 | 10 | 10 | 33 |
| Method[4] | Drop-in | Drop-in | Premix | Drop-in |

TABLE II

| Product[1] | Wt % Yield Example # | | | | |
|---|---|---|---|---|---|
| | 5 | 6 | 7 | 8 | 9 |
| Methane | 0.1 | 0.1 | 0.1 | 0.2 | 0.5 |
| Ethane | 0.1 | 0.2 | 0.2 | 0.5 | 1.4 |
| Ethylene | 0.1 | 0.3 | 0.7 | 2.6 | 4.1 |
| Propane | 0 | 0.1 | 0.1 | 0.3 | 0.2 |
| Propylene | 0.8 | 1.8 | 2.0 | 4.4 | 5.6 |
| Acetaldehyde | 0.9 | 0.9 | 0.8 | 1.7 | 2.3 |
| Propionaldehyde | 13.9 | 38.5 | 59.9 | 43.3 | 31.7 |
| Acetone | 0.3 | 1.0 | 1.4 | 2.4 | 2.5 |
| 1,4-Dioxane | 1.8 | 3.1 | 0.95 | 0.5 | 0.1 |
| Propylene Oxide | 0 | 0 | 0 | 0 | 0 |
| n-propanol | 0.45 | 0.7 | 0.4 | 0.2 | 0.06 |
| i-propanol | 0 | 0.02 | Trace | Trace | Trace |
| Propylene Glycol | 0.6 | 1.3 | 1.1 | 0.9 | 0.2 |
| Dipropylene Glycol | 2.4 | 2.2 | 2.2 | 2.0 | 0.5 |
| Dioxalane | 0.6 | 2.6 | 4.1 | 1.5 | 0.5 |
| Lower MW Polyols[2] | 76.2 | 39.8 | 20.3 | 34.2 | 38.0 |
| G.C. lights[3] | 0 | 4.8 | 5.1 | 4.2 | 6.2 |
| $CO_2$ | 0.4 | 0.5 | 0.2 | 0.9 | 5.4 |
| Coke | 2.0 | 2.1 | 0.4 | 0.2 | 0.7 |
| Catalyst | A | A | A | A | A |
| Temp, °C. | 250 | 250 | 350 | 550 | 650 |
| Vol % Steam | 0 | 10 | 10 | 10 | 10 |

TABLE II-continued

| | Wt % Yield Example # | | | | |
|---|---|---|---|---|---|
| Product[1] | 5 | 6 | 7 | 8 | 9 |
| in N₂ Stream | | | | | |
| Method[4] | Drop-in | Drop-in | Drop-in | Drop-in | Drop-in |

TABLE III

| | Example # Wt % Yield | | | |
|---|---|---|---|---|
| Product[1] | 10 | 11 | 12 | 13 |
| Methane | 0.1 | Trace | 0.1 | 0.1 |
| Ethane | Trace | 0.1 | 0.3 | 0.3 |
| Ethylene | 1.6 | 1.5 | 0.8 | 0.4 |
| Propane | 1.5 | 4.1 | 1.0 | 0.1 |
| Propylene | 4.2 | 3.1 | 5.9 | 2.4 |
| Acetaldehyde | 0.4 | 0.7 | 1.9 | 0.6 |
| Propionaldehyde | 14.1 | 16.7 | 66.6 | 26.7 |
| Acetone | 1.3 | 0.7 | 1.6 | 1.0 |
| 1,4-Dioxane | 0.8 | 0.4 | 0.8 | 0.1 |
| Propylene Oxide | 0 | 0 | 0 | 0 |
| n-propanol | 0.8 | 0.9 | 0.4 | 0.2 |
| i-propanol | Trace | Trace | 0 | Trace |
| Propylene Glycol | 2.6 | 0.1 | 0.6 | 0.9 |
| Dipropylene Glycol | 1.2 | 0.1 | Trace | 0.02 |
| Dioxalane | 0.2 | 0 | 0 | 0.8 |
| Lower MW Polyols[2] | 52.9 | 59.7 | 14.9 | 57.7 |
| G.C. lights[3] | 4.2 | 4.6 | 3.7 | 7.4 |
| CO₂ | 0.6 | 0.8 | 0.7 | 0.6 |
| Coke | 13.5 | 6.5 | 0.7 | 0.7 |
| Catalyst | SAPO-34 | SAPO-5 | SAPO-11 | Mg-APSO-31 |
| Temp, °C. | 450 | 450 | 450 | 450 |
| Vol % Steam in N₂ Stream | 10 | 10 | 10 | 10 |
| Method[4] | Pre-mix | Pre-mix | Pre-mix | Drop-in |

TABLE IV

| | Example # Wt % Yield | | | |
|---|---|---|---|---|
| Product[1] | 14 | 15 | 16 | 17 |
| Propionaldehyde | 24 | 43.5 | 36.9 | 27.0 |
| Acetone | 4 | 0.9 | 1.1 | 1.6 |
| Propionic Acid | Trace | 1.3 | 2.2 | 3.8 |
| Propylene Oxide | 0 | 0.09 | 0 | 0.01 |
| n-propanol | 1 | 4.9 | 6.7 | 3.9 |
| i-propanol | 0 | 0.03 | 0.02 | 0.06 |
| Propylene Glycol | Trace | 8.2 | 12.7 | 13.7 |
| Dipropylene Glycol | Trace | 5.3 | 3.3 | 7.8 |
| Dioxolanes + Dioxanes | 64 | 26.2 | 28.1 | 29.5 |
| Coke | 0.5 | 1.5 | 1.6 | 2.3 |
| Catalyst | A | A | A | A |
| Temp, °C. | 500 | 200 | 230 | 210 |
| Vol % Steam in N₂ Stream | 0 | 10 | 33 | 33 |
| Method[4] | Pre-mix | Pre-mix | Pre-mix | Drop-in |

Footnotes for TABLES I through IV

1. Wt % yield, products determined by g.c. analyses with external standardization; $CO_2$ and coke were analyzed by TCD. The other hydrocarbons, excluding the lower MW polyols, were analyzed by FID.
2. The wt % yield of lower MW polyols was calculated by subtracting the sum of all other yields from 100. The lower MW polyols consisted primarily of PG through the penta-propylene glycols.
3. The g.c. lights consisted of 2-ethyl-4-methyl-1,3-dioxolane, dimethyl-1,4-dioxane, and 2-methyl-2-pentenal.
4. In the drop-in method, the fluid bed reactor was brought to run conditions with an upward flow of $N_2$ (100 cc/min) except Table IV where the upward $N_2$ flow was 300 cc/min. The polyol (Ave MW 440) was dropped into the fluid bed via a rotating addition spoon. The run length was 20 minutes. In the pre-mix method, the polyol was pre-mixed with the catalyst and then placed into the tubular fluid bed reactor which was heated to the reaction temperature over 30 minutes and then held at reaction conditions for an additional 5 minutes. Catalytic runs employed 4 grams of catalyst and 0.4 g of polyol.

The Table I data demonstrates the usefulness of catalysts for converting polyols to light products, especially to propionaldehyde. The pre-mix method appears to be more efficient in converting the polyol, including lower MW polyol, to propionaldehyde. This may be due to better contact between the feed and the catalyst. Addition of 10 vs. 33 mol % steam to the nitrogen feed is preferred. The lower mol % steam may minimize saturation of the catalyst's active sites with absorbed water as opposed to polyol and its derivatives. Catalyst A contains approximately 15 wt % HZSM-5 and 3 wt % P within a binder.

The Table II data demonstrates the usefulness of adding 10 mole % steam to the nitrogen feed. The steam may increase the number of Brönstead acid sites and thus the catalyst's activity. An optimal temperature of 350° C. to 450° C. is demonstrated.

The Table III data demonstrates that SAPOs and metal-APSOs may be used in place of HZM-5.

The Table IV data demonstrate that lower reaction temperatures and the use of steam favor production of propylene glycol and dipropylene glycol which are extremely valuable products.

We claim:

1. A process for reclaiming a polyether polyol comprising the steps of:
   a) Contacting particles of the polyether polyol and a zeolite containing particulate catalyst in a fluidized bed reaction zone at a temperature effective to produce a volatile organic component, and a spent catalyst component;
   b) Withdrawing a first stream comprising the volatile organic component from the reaction zone;
   c) Withdrawing a second stream comprising spent catalyst from the reaction zone; and d) Heating the second stream in a regeneration zone in the presence of oxygen at a temperature effective to regenerate the catalyst.

2. The process of claim 1 wherein the process is performed in a continuous manner.

3. The process of claim 1 wherein the zeolite containing particulate catalyst has an average particle diameter of from about 10 to 150 microns.

4. The process of claim 1 wherein the zeolite component of the zeolite containing particulate catalyst is selected from the group consisting of ZSM-4, ZSM-5, ZSM-11, ZSM-12, ZSM-22, ZSM-23, ZSM-34, ZSM-35, ZSM-38, ZSM-48, ZSM-50, erionite, offretite, mordenite, faujasite, zeolite L, zeolite beta, zeolite Y, zeolite X, SAPOs and APSOs with or without metal substitution, and mixtures thereof.

5. The process of claim 1 wherein the zeolite component of the zeolite containing particulate catalyst is a Group VA or boron containing zeolite.

6. The process of claim 1 wherein steam is fed to the reaction zone.

* * * * *